United States Patent [19]

Shu

[11] Patent Number: 5,415,325
[45] Date of Patent: May 16, 1995

[54] DROPPER-CONTROLLER WITH AN AUTOMATICALLY SEALING MEANS

[76] Inventor: Han C. Shu, 5th Fl., No. 205, Wu Shin Street, Taipei, Taiwan, Prov. of China

[21] Appl. No.: 287,901

[22] Filed: Aug. 9, 1994

[51] Int. Cl.⁶ .................................. A61M 5/16
[52] U.S. Cl. ................................ 222/66; 604/254; 604/127; 137/399
[58] Field of Search .............. 222/66; 604/127, 254; 137/399

[56] References Cited

U.S. PATENT DOCUMENTS

| | | | |
|---|---|---|---|
| 2,074,927 | 3/1937 | Logette et al. | 222/66 |
| 3,216,419 | 11/1965 | Scislowicz | 137/399 X |
| 3,227,173 | 1/1966 | Bernstein | 604/254 X |
| 4,640,306 | 2/1987 | Fan | 137/399 X |
| 4,870,987 | 10/1989 | Cheng | 137/399 X |
| 4,959,053 | 9/1990 | Jang | 604/254 X |
| 5,234,414 | 8/1993 | Hung | 604/254 |

FOREIGN PATENT DOCUMENTS 77205813 10/1989 China.
712094 1/1980 ........................................ 604/254

Primary Examiner—Andres Kashnikow
Assistant Examiner—Kenneth Bomberg
Attorney, Agent, or Firm—Browdy and Neimark

[57] ABSTRACT

A dropper-controller including a reservoir connected with a dropper bottle containing a liquid medicine, and an automatically sealing member formed by a cup-like buoyage and disposed in the reservoir. When the liquid medicine gradually drops from the dropper bottle into the reservoir, the buoyage is buoyed up and automatically open a lower discharging opening of the reservoir, permitting the liquid medicine to flow through a hose to an injection needle for injection. When the liquid medicine in the dropper bottle is about exhausted, the level of the liquid medicine in the reservoir descends, making the buoyage together move downward onto the discharging opening of the reservoir and seal the same so as to interrupt the passage of the liquid medicine.

2 Claims, 6 Drawing Sheets

DROPPER-CONTROLLER WITH AN AUTOMATICALLY SEALING MEANS

BACKGROUND OF THE INVENTION

The present invention relates to a controller for a medical dropper, and more particularly to a dropper-controller with an automatically sealing means, which has simple structure and is manufactured at low cost while able to more effectively seal the passage of the liquid flow.

A medical dropper has a controller for guiding a liquid medicine contained in a dropper bottle of the dropper to a syringe which injects the liquid medicine into human body.

FIG. 1 shows a conventional controller of the medical dropper, which includes a sharp connector 91 inserted into the dropper bottle to guide the liquid medicine into a reservoir 92. The liquid medicine is further guided through a hose 93 to a controller member 94 which is disposed on the hose 93 to control the amount of the flowing liquid medicine or shut off the flow.

Such controller is totally manually operated so that in case of negligence, the controller will be still opened after the liquid medicine is exhausted. This will cause air to be injected into human body and result in great danger.

Moreover, FIG. 2 shows another conventional dropper in which a membrane 96 is disposed over a lower opening of a cylindric reservoir 95 containing liquid medicine. When the membrane 96 is buoyed up by the liquid medicine, the same is permitted to flow out of the reservoir through the lower opening thereof. However, when the liquid medicine is exhausted, the membrane 96 descends to block the opening and thus prevent air from entering human body.

Although the controller of the dropper shown in FIG. 2 is able to prevent air from entering human body after the liquid medicine is exhausted, the structure of such controller is quite complicated. For example, it is complicated to fix one side of the membrane beside the opening of the reservoir. Therefore, the manufacturing cost of such controller is increased and the price thereof is relatively high. Especially, such controller includes more parts and has larger volume so that after discarded, such controller is liable to cause more serious contamination to the environment.

Taiwan Patent Application No. 77205813 entitled " an automatic dropper-controller" discloses a technique of installation of a buoyage in the dropper bottle. A guiding lever is disposed at a top end of the buoyance and a controlling lever is disposed at a bottom end thereof and extends into a discharging passage. In addition, a ring member is fixed in the dropper bottle and at the upper end of the buoyage in order to effectively prevent the buoyage from ascending and seal an opening of the discharging passage.

According to such arrangements, the buoyage is a solid member made of relatively much material and an additional ring member is necessary to be disposed in the dropper bottle. The assembling operation of the buoyage and the ring member complicates the manufacturing procedure of the dropper.

SUMMARY OF THE INVENTION

It is therefore a primary object of the present invention to provide a dropper-controller with an automatically sealing means. The dropper-controller includes a reservoir connected with a dropper bottle containing a liquid medicine, and an automatically sealing means formed by a cup-like buoyage and disposed in the reservoir. When the dropper-controller is not used and the reservoir is empty, the buoyage is located over a lower discharging opening of the reservoir and block the same due to the gravity. While when the liquid medicine gradually drops from the dropper bottle and fills up the reservoir, the buoyage is buoyed up by the liquid medicine in the reservoir and automatically open the lower discharging opening of the reservoir, permitting the liquid medicine to flow through a hose to an injection needle for injection. When the liquid medicine in the dropper bottle is about exhausted, some liquid medicine remains in the cup-like buoyage to increase the weight thereof, whereby as the level of the liquid medicine in the reservoir descends, the buoyage moves downward along therewith onto the discharging opening of the reservoir and automatically seal the same so as to prevent air from being injected into human body.

It is a further object of the present invention to provide the above dropper-controller which has simple structure and is easily manufactured. During the manufacturing procedure, an operator only needs to place the cup-like buoyage into the reservoir without other complicated assembling steps. Especially, the present dropper-controller is manufactured with less material than the conventional dropper-controller which employs a membrane as the sealing means so that the manufacturing cost is reduced and the price can be lowered. Moreover, the medical wastes result from the used and discarded members are reduced and the contamination thereof to the environment is minimized. In addition, the present dropper-controller is different from the above membrane-employing dropper-controller in the sealing manner. In the membrane-employing dropper-controller, the membrane is fixedly located on the discharging opening, while the cup-like buoyage of the present invention is naturally located on the discharging opening by gravity. The sealing force of the membrane is about 0.05 gw and smaller than the sealing force of the present invention which is about up to 2 gw.

The present invention can be best understood through the following description and accompanying drawing, wherein:

BRIEF DESCRIPTION OF THE DRAWINGS

FIG. 8 is still a sectional view according to FIG. 3, wherein the liquid medicine contained in the reservoir is totally discharged and the buoyage descends to block the lower opening of the reservoir.

DETAILED DESCRIPTION OF THE PREFERRED EMBODIMENTS

Figure 1:
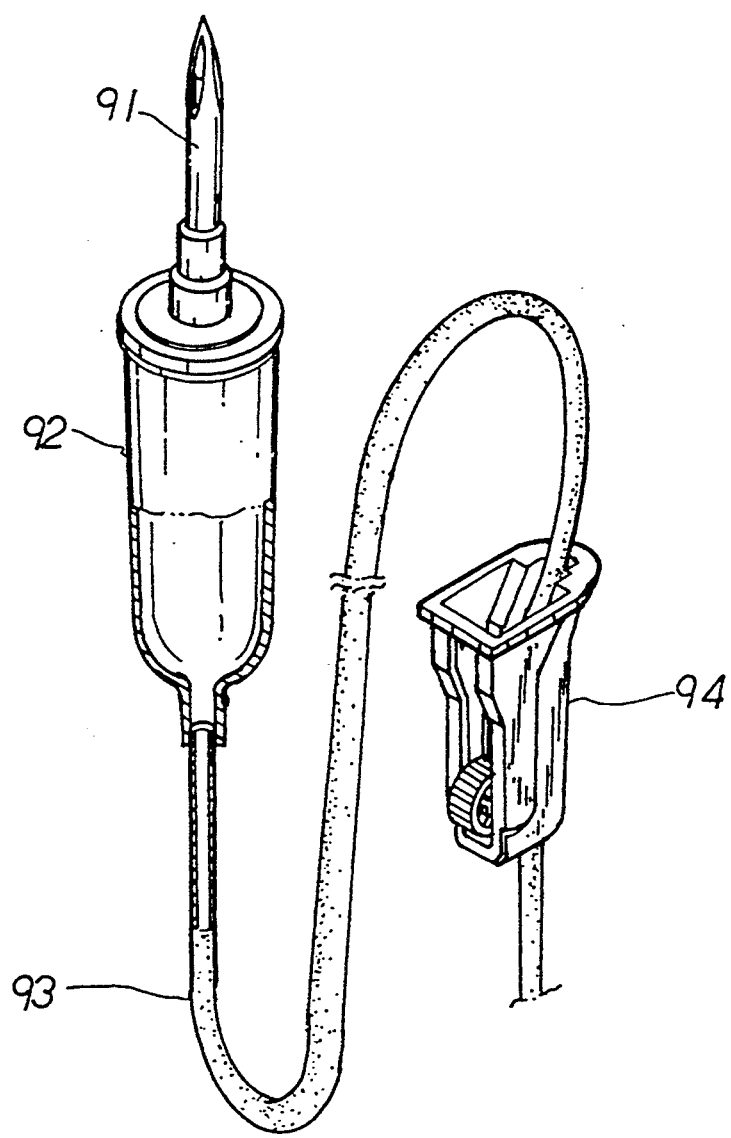
FIG. 1 is a perspective view of a conventional dropper-controller.
Figure 2:
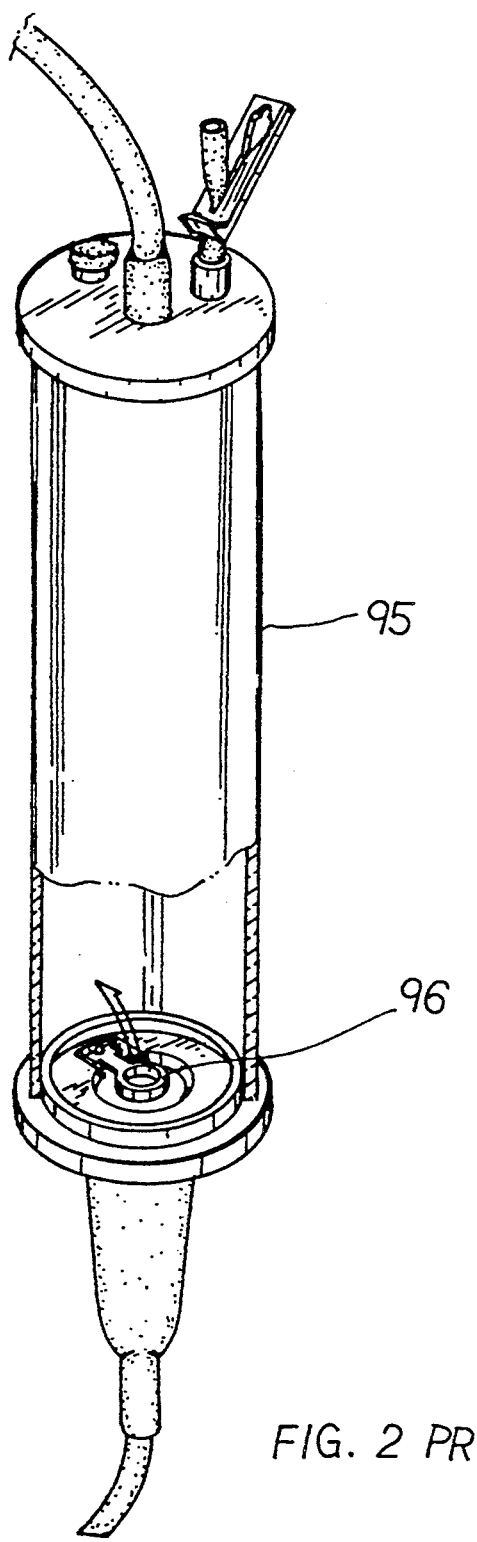
FIG. 2 shows another conventional dropper-controller which includes a membrane for sealing an opening of a dropper bottle.
Figure 3:
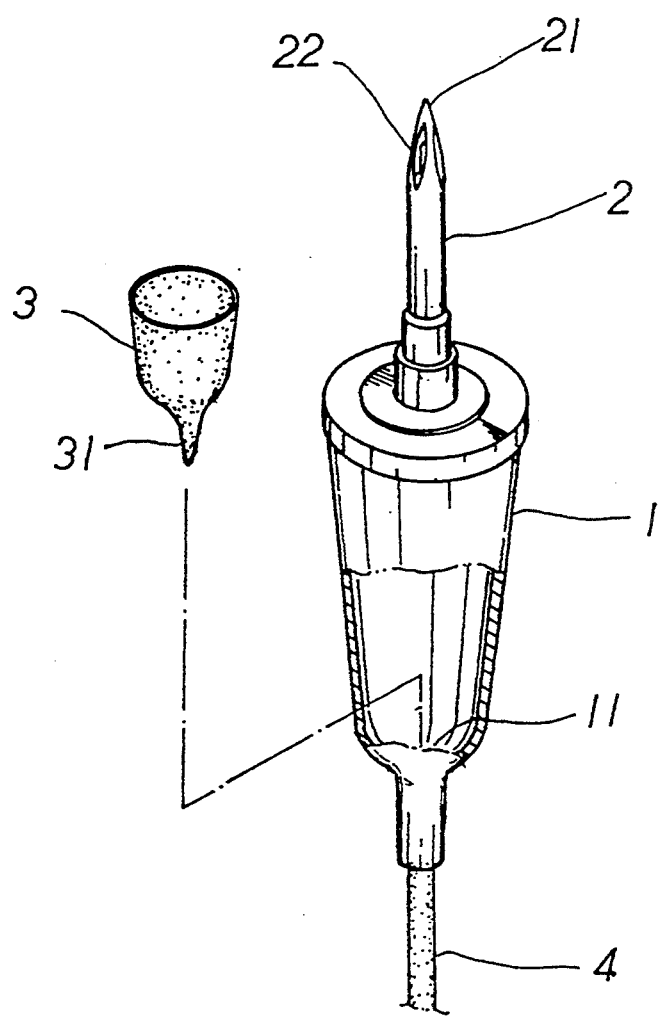
FIG. 3 is a perspective view of a preferred embodiment of the present invention with the reservoir partially sectioned and the cup-like buoyage separated therefrom.

Please refer to FIG. 3. The dropper-controller of the present invention includes a reservoir 1 preferably made of transparent material for observing the dropping of a liquid medicine and a hollow connecting pipe 2 having a sharp top end 21 for inserting into a dropper bottle and guiding the liquid medicine contained therein through an entrance hole 22 of the sharp top end 21 into the reservoir 1. The reservoir 1 has a tapered bottom end formed with a discharging opening 11 ( referring to FIG. 4 or 5 ), whereby the liquid medicine contained in the reservoir 1 can flow out into a guiding hose 4 connected with an injection needle at a distal end thereof (not shown).

Figure 4:
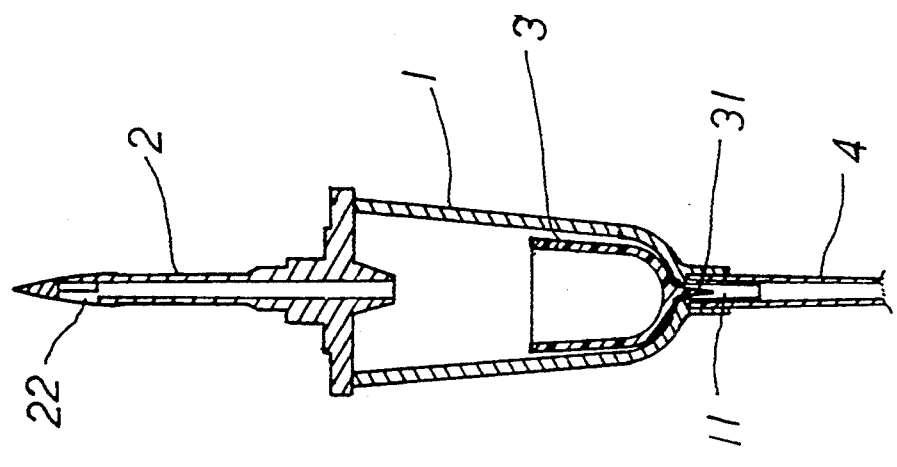
FIG. 4 is a sectional view according to FIG. 3, wherein the reservoir is empty and the cup-like buoyage is located over a lower opening thereof.

A cup-like buoyage 3 is disposed in the reservoir 1, having an upper opening for receiving the liquid medicine incoming from the connecting pipe 2 and a lower pin portion 31 downward extending from a bottom of the buoyage 3. The maximum outer diameter of the buoyage 3 is slightly smaller than the minimum inner diameter of the reservoir 1, whereby the buoyage 3 can freely float on the liquid medicine and move up and down along therewith. As shown in FIG. 4, when the reservoir 1 is empty and the buoyage 3 is located on the bottom thereof, the pin portion 31 of the buoyage 3 extends into the discharging opening of the reservoir 1 and seals the same.

It is known from FIG. 4 that the entrance hole 22 of the connecting pipe 2 communicates with the interior thereof so as to guide the liquid medicine to flow through the connecting pipe 2 and stably drop into the reservoir 1.

Figure 5:
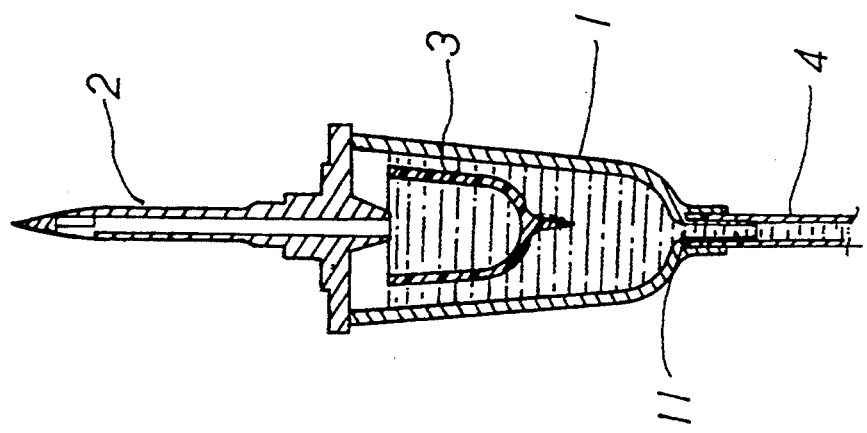
FIG. 5 is still a sectional view according to FIG. 3, wherein the reservoir is filled with liquid medicine and the buoyage is buoyed up.
Figure 6:
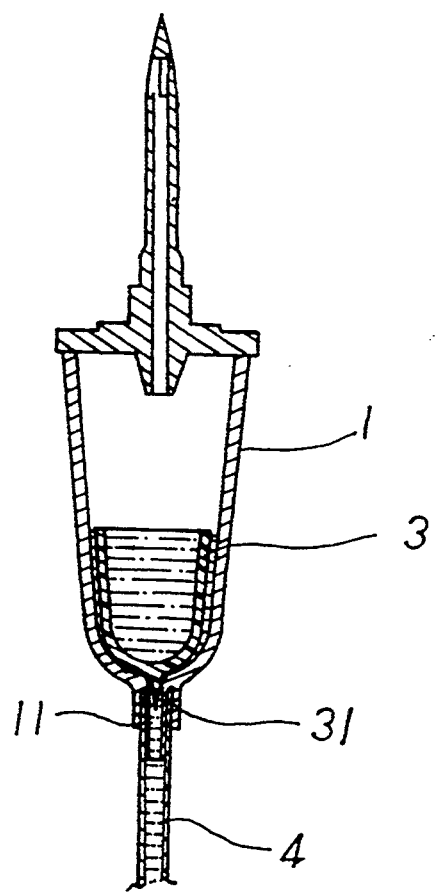

After the connecting pipe 2 is inserted into the dropper bottle, the liquid medicine is guided into the reservoir 1 drop by drop in such a manner that the liquid medicine first drops into the buoyage 3 and then, after the buoyage 3 is filled up with the liquid medicine, the same spills out of the buoyage 3 and flows into the reservoir 1. After the reservoir 1 is gradually filled up with the liquid medicine, the buoyage 3 suffers the buoyance of the liquid medicine and moves up along with the ascending level of the liquid medicine. At this time, the lower pin portion 31 of the buoyage 3 leaves the discharging opening 11 of the reservoir 1, permitting the liquid medicine to flow out through therethrough as shown in FIG. 5. The flowing out liquid medicine goes through the hose 4 to the needle to be injected into human body.

When the liquid medicine gradually flows out of the reservoir 1 through the discharging opening 11 thereof, the level of the liquid medicine descends and the buoyage 3 moves downward as well along with the descending level until the pin portion 31 again plugs into the discharging opening 11 and seals the same. At this time, the air is prevented from going into the hose 4 and human body. Meanwhile, some liquid medicine remains in the bottom of the reservoir 1. The level of the remaining liquid medicine is substantially identical to that of the top of the buoyage 3. The remaining liquid medicine more surely prevents the air from being injected into human body. In addition, some other liquid medicine remains in the buoyage 3. Since the density of the liquid medicine is greater than that of the material for manufacturing the buoyage 3, the weight of the cup-like buoyage 1 filled with the liquid medicine will be greater than that of a solid buoyage. Therefore, the cup-like buoyage 3 exerts a greater engaging force approximately up to 2 gw) on the bottom of the reservoir 1 and thus the discharging opening 11 is more tightly sealed by the pin portion 31 of the buoyage 3 and the air is more reliably prevented from passing through the discharging opening 11 and entering human. Accordingly, the dropper-controller of the present invention can achieve a sealing effect better than that of the conventional dropper-controller which employs a membrane as the sealing means.

The present invention only additionally includes a cup-like buoyage to achieve the automatically sealing effect. Especially, during manufacturing procedure, an operator only needs to place the buoyage into the reservoir without other complicated assembling steps. Therefore, the manufacturing cost is greatly reduced. Moreover, because the present invention is manufactured with less material, the medical wastes result from the used and discarded members are reduced and the contamination thereof to the environment is minimized.

Moreover, the pin portion 31 of the cup-like buoyage 3 serves to smoothly guide the buoyage 3 to descend onto the discharging opening 11 and seal the same. Such operation is more reliable than that of the conventional controller in which the membrane is solely controlled by the buoyancy of the liquid medicine.

The present invention is greatly different from the device disclosed in Taiwan Patent Application No. 77205813 in that after the liquid medicine substantially completely drops out of the reservoir 1, the cup-like buoyage 3 of the present invention still fully contains some liquid medicine and has a weight greater than that of the solid buoyage of the above prior art. Therefore, the sealing force exerted on the discharging opening 11 of the cup-like buoyage 3 of the present invention is much greater than that of the solid buoyage of the prior art. Accordingly, the present invention is apparently advantageous over the prior art in reliability of the automatically sealing effect.

Figure 7:
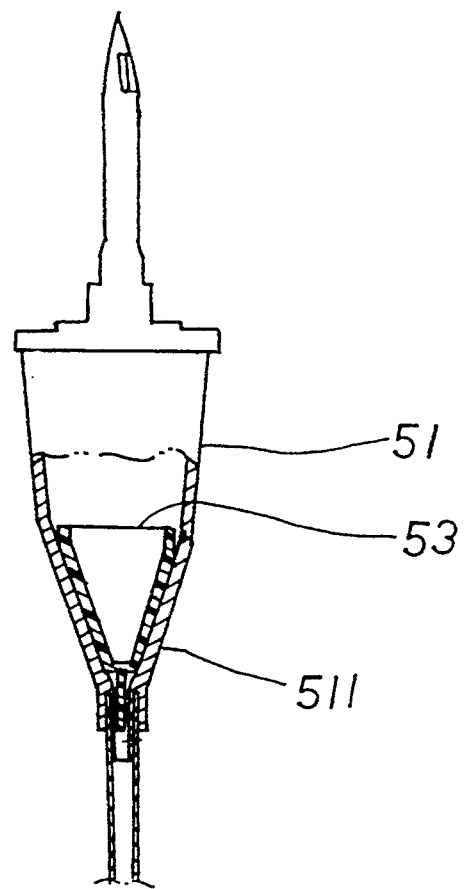
FIG. 7 is a sectional view of another preferred embodiment of the present invention, wherein the buoyage and the bottom of the reservoir are conic.

FIG. 7 shows another embodiment of the present invention, wherein the reservoir 51 has a conic bottom portion 511 and the buoyage 53 is conically shaped corresponding to the bottom portion 511 and adapted to freely float on the surface of the liquid medicine and ascend/descend along therewith. Such arrangement permits the buoyage 53 to even more smoothly and effectively automatically sealing the discharging opening of the reservoir 51.

It is to be understood that the above description and drawings are only used for illustrating one embodiment of the present invention, not intended to limit the scope thereof. Any variation and derivation from the above description and drawings should be included in the scope of the present invention.

What is claimed is:

1. A dropper-controller with automatically sealing means, comprising:
a reservoir having an upper connecting pipe adapted to connect with a dropper bottle and guide a liquid medicine contained therein into said reservoir, and a lower discharging opening connected with a guiding hose a distal end of which is connected with an injection needle; and
a sealing means formed by a cup-like buoyage and disposed in said reservoir, said cup-like buoyage being adapted to float on an upper surface of the liquid medicine and ascend/descend along therewith, said cup-like buoyage having an upper opening for receiving the liquid medicine dropping from said connecting pipe and a bottom formed with a downward extending pin portion, said pin portion being adapted to plug into said discharging opening of said reservoir and seal the same.

2. A dropper-controller as claimed in claim 1, wherein said bottom of said reservoir is conic and said cup-like buoyage is conic corresponding to said bottom of said reservoir.

* * * * *